United States Patent [19]

Merten et al.

[11] Patent Number: 4,665,190

[45] Date of Patent: May 12, 1987

[54] HETEROCYCLIC TRIS-HYDROXYALKYL COMPOUNDS

[75] Inventors: Rudolf Merten, Leverkusen; Ludwig Rottmaier, Odenthal, both of Fed. Rep. of Germany

[73] Assignee: Bayer Aktiengesellschaft, Leverkusen, Fed. Rep. of Germany

[21] Appl. No.: 307,538

[22] Filed: Oct. 1, 1981

Related U.S. Application Data

[63] Continuation of Ser. No. 126,419, Mar. 3, 1980, abandoned.

[30] Foreign Application Priority Data

Mar. 6, 1979 [DE] Fed. Rep. of Germany ....... 2908627

[51] Int. Cl.⁴ .......................................... C07D 249/12
[52] U.S. Cl. .................................................. 548/264
[58] Field of Search ......................................... 548/264

[56] References Cited

U.S. PATENT DOCUMENTS 3,737,432  6/1973  George et al. ..................... 544/222

FOREIGN PATENT DOCUMENTS 1104965  4/1961  Fed. Rep. of Germany ...... 548/264
2156972  6/1973  France ............................... 548/264

OTHER PUBLICATIONS

Chemical Abstracts Chemical Substance Index, 9th Collective Index, 1972–1976, p. 39193CS (1978), QDIA51.
Chemical Abstracts Ninth Collective Index, pp. 39006CS and 39136CS. (1978).

*Primary Examiner*—Glennon H. Hollrah
*Assistant Examiner*—D. L. Dinner
*Attorney, Agent, or Firm*—Connolly & Hutz

[57] ABSTRACT

New tris-hydroxyalkyl triazolidine-3,5-diones are obtained by reacting triazolidine-3,5-dioxy with alkylene oxides.

3 Claims, No Drawings

HETEROCYCLIC TRIS-HYDROXYALKYL COMPOUNDS

This application is a continuation of application Ser. No. 126,419 filed Mar. 3, 1980 now abandoned.

The present invention relates to heterocyclic tris-hydroxyalkyl compounds and to a process for the production. According to the present invention new heterocyclic triols corresponding to the following general formula (I)

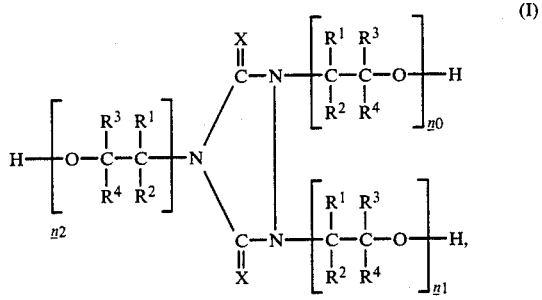

are provided, wherein $n_0$, $n_1$ and $n_2$ are the same or different and each is an integer of from 1 to 30 and preferably of from 1 to 10, and $R^1$, $R^2$, $R^3$ and $R^4$ are the same or different and each is a hydrogen atom, an optionally halogen-substituted aliphatic, preferably with $C_1$–$C_{10}$, cycloaliphatic, preferably with $C_4$–$C_8$ or araliphatic, preferably with $C_7$–$C_{17}$ radical, or an aromatic, preferably with $C_6$–$C_{16}$ radical optionally substituted by halogen atoms, alkyl groups and/or alkoxy groups. Each of $R^1$, $R^2$, $R^3$ and $R^4$ more preferably represents a hydrogen atom, an optionally halogen (chlorine, bromine)—substituted $C_1$–$C_4$ alkyl radical, most preferably methyl and ethyl, or optionally by a $C_1$–$C_4$ alkyl radical, by halogen atoms (chlorine, bromine) and/or by a $C_1$–$C_4$ alkoxy group substituted aryl radical, most preferably phenyl, and X is O or S, preferably O.

The radicals are, with particular preference, derived from ethylene and propylene oxide units having a degree of alkoxylation n of 1.

The triols according to the present invention which correspond to general formula (I) above are new and are obtained by reacting triazolidine-3,5-dione (=uracol) with alkylene oxides, preferably ethylene oxide, propylene oxide, butylene oxide, ir styrene oxide, optionally in the presence of a suitable catalyst. However, it is also possible to use the thione analogs of uracol. The addition of the alkylene oxide to the three NH-groups of the triazolidine-3,5-dione may be carried out in the presence of both acid and alkaline catalysts. However, the triols corresponding to formula (I) above are preferably produced in the presence of basic catalysts, such as tetra-ethyl ammonium chloride, tertiary amines, such as triethyl amine and dimethyl aniline, and alkali or alkaline earth hydroxides or their carbonates, such as calcium hydroxide or potassium carbonate. However, it is also possible to use alkali halides, such as lithium chloride. The catalyst is preferably used in a quantity of from 0.05 to 3% based on the reactants.

According to one preferred embodiment, three moles of ethylene oxide are added to one mole of uracol in the absence of a catalyst, resulting in the substantially quantitative formation of N,N',N''-tris-hydroxyethyl uracol.

This reaction is all the more suprising insofar as, in view of their different basicity, the three NH groups of the uracol should show different reactivity, with the result that the ethylene oxide would had been expected to react with already existing hydroxyl groups to form polyether structural units. The reaction of the ethylene oxide to the uracol may be followed easily in the absence of a catalyst because, after the consumption of three moles of ethylene oxide, no more ethylene oxide is taken up under normal pressure. The tris-hydroxy compounds corresponding to formula (I) are preferably produced using equivalent quantities, such as 3 ($n_0+n_1+n_2$) moles of alkylene oxide per mole of uracol.

The triazolidine-3,5-dione used for producing the new triols corresponding to formula (I) is known from the literature and may be obtained for example by heating hydrazine-N,N'-dicarboxylic acid diamide to a temperature above 200° C. under the elimination of ammonia.

The reaction of the uracol with the alkylene oxide is preferably carried out in inert organic solvent although other inert solvents may be used. Particularly suitable solvents are polar organic solvents, such as dimethyl sulfoxide, tetramethylene sulphone, dimethyl formamide, dimethyl acetamide and N-methyl-2-pyrrolidone. Another very suitable solvent is water. In this latter case, there is surprisingly no reaction between the alkylene oxide, preferably ethylene oxide and the water. It is not absolutely essential to react the uracol in solution with the alkylene oxide, since the reaction may also be carried out with uracol suspension, in which case the triol dissolves into a solution so that the end of the reaction is indicated by the presence of a clear solution. Uracol and alkylene oxide may also be added together to the triol solution formed so that the quantity of solvent can be kept very small. For economic reasons, the quantity of solvent used should preferably be very small and may amount to between 0.3 part by weight and 20 parts by weight of solvent per part by weight of reactants. On completion of the reaction, the solvent may be removed by applying a vacuum and the viscous residue left may be purified by working up in the usual way, for example by recrystallisation. In many cases, however, there is no need for purification and the crude product can be immediatly further processed as such.

The reaction is preferably carried out at temperatures of from 25° C. to 200° C. and, with particular preference, at temperatures of from 80° C. to 150° C.

The reaction times are generally between 30 minutes and several days although, in special cases, they may be longer or shorter. By adjusting the reaction conditions suitably, for example by altering the pressure, it is possible to obtain shorter reaction times.

In one particularly preferred embodiment, uracol is reacted with ethylene oxide in a lower dialkyl formamide (for example dimethyl formamide) at a temperature of 120° C. After reaction, the solvent is removed in a water jet vacuum and the reaction mixture is concentrated at 90° to 100° C./0.2 mbar until constant in weight. The viscous residue formed crystallises very rapidly and, after suspension in for example ethanol or isopropanol, may be filtered off under suction. The substantially pure tris-2-hydroxyethyl triazolidine-3,5-dione obtained may be further purified by recrystallisation from e.g. acetone or isopropanol.

The tris-2-hydroxyalkyl triazolidine diones corresponding to formula (I) above are valuable starting products for the production of polymeric compounds. They may be incorporated as crosslinking agents into known polyesters containing hydroxyl groups, for example adipic acid and phthalic acid diglycol, and maybe used for the production of rigid or flexible polyurethane foams.

The compounds according to the present invention which correspond to formula (I) above, particularly those in which each n=1, may be used as starters for the production of polyethers containing hydroxyl groups which may in turn be used for the production of rigid or flexible polyurethane foams, depending upon their molecular weight.

EXAMPLE 1

50.5 g (0.5 mole) of uracol is dissolved in 150 ml of dimethyl formamide in a 500 ml three-necked flask equipped with a stirrer, a thermometer and a water-cooled reflux condenser. 66 g (1.5 moles) of ethylene oxide is introduced into this solution at 120° C. in such a way that no ethylene oxide escapes through a bubble counter fitted to the reflux condenser. On completion of the reaction, the reaction mixture is concentrated in vacuo, ultimately at 100° C./0.2 mbar, until constant in weight. 117 g of a viscous liquid is thus obtained. According to a gas chromatogram, this liquid contains more than 85% of the pure tris-hydroxyethyl triazolidine-3,5-dione which, on standing, gradually crystallises out from the viscous residue. The pure tris-hydroxyethyl triazolidine-3,5-dione melting at 90° C. is also obtained by dissolving the viscous crude product in isopropanol and crystallising the resulting solution by cooling. IR- and NMR-spectra and elemental analysis confirm the assumed structure.

Calculated: 41.2% C, 6.4% H, 18% N, 21.9% OH, Observed: 41.4% C, 6.5% H, 17.9% N, 21.7% OH.

EXAMPLE 2

1000 g of propylene oxide is added at 105° C. to a mixture of 303 g (3 moles) of uracol, 30 g powdered caustic soda and 450 ml of dimethyl formamide in a pressure vessel in such a way that the internal pressure thereof does not rise above 8 bars. On completion of the reaction, the volatile constituents are removed in vacuo, ultimately at 100° C./0.2 mbar. The residue is dissolved in chloroform and neutralised with dilute $H_2SO_4$. The sodium sulphate thus precipitated is filtered off and the solvent is removed in vacuo until the product is constant in weight. 1272 g (97.7% yield) of a yellowish, oily polyether having a viscosity $\eta 25$ of 8692 mPa.s is obtained, the IR-spectrum thereof coinciding with the assumed structure. Analysis revealed a hydroxyl content of 12% (calculated: 12.1%) and a nitrogen content of 9.8% (calculated 9.9%).

EXAMPLE 3

50.5 g (0.5 mole) of uracol is dissolved in 150 ml of dimethyl formamide in a three-necked flask equipped with a stirrer, a thermometer and a reflux condenser, followed by the addition of 2.5 g of tetra-ethyl ammonium chloride. 108 g of isobutylene oxide are added dropwise to the resulting mixture at 120° C., followed by stirring for 2 hours at 120° C. After the volatile constituents have been removed in vacuo, ultimately at 100° C./0.2 mbar, 158 g of a pale yellow, viscous residue is obtained, the IR-spectrum thereof coinciding with the assumed structure. Analysis revealed a hydroxyl content of 15.9% OH (calculated 16.1% OH), whilst elemental analysis produced the following values:

calculated: 53.0% C, 8.52% H, 13.25% N, observed: 52.8% C, 8.44% H, 13.5% N.

EXAMPLE 4

50.5 g (0.5 mole) of uracol is dissolved in 150 g of water in a three-necked flask equipped with a stirrer, a thermometer and a reflux condenser. Following the addition of 0.5 g of endoethylene piperazine, 66 g (1.5 moles) of ethylene oxide is introduced with refluxing of the solvent in such a way that no ethylene oxide escapes. On completion of the reaction, the reaction mixture is concentrated in vacuo, ultimately at 80° C./0.2 mbar, until constant in weight. 115 g of a viscous liquid is thus obtained. According to a gas chromatogram, this liquid contains approximately 75% of the pure tris-hydroxyethyl triazolidine-3,5-dione.

EXAMPLE 5

Following the general procedure of Example 4, 50.5 g of uracol is dissolved in 150 g of dimethyl formamide, 0.75 g of lithium chloride is added and the solution is reacted with 66 g of ethylene oxide. Concentration of the reaction mixture gives 114 g of a viscous liquid which begins to crystallise after a few hours and which, according to a gas chromatogram, contains 82% of pure tris-hydroxyethyl triazolidine-3,5-dione.

EXAMPLE 6

In a three-necked flask equipped with a stirrer, a thermometer and a reflux condenser cooled with a mixture of dry ice and methanol, 101 g (10 moles) of uracol is suspended in 1000 g of dimethyl formamide 30 g of triethyl amine is added to the resulting suspension. A total of 1320 g of ethylene oxide is then introduced at 120° C. in such a way that a gentle reflux is initiated and the reaction, which has meanwhile become highly exothermic, can be kept at a temperature of 120° C. by cooling with air. On completion of the reaction, the reaction mixture is concentrated in vacuo, ultimately at 80° C./0.2 mbar, until constant in weight. 2330 g of a viscous solution is obtained. By the following day, this solution had completely crystallised and, according to analysis by gas chromatography, contains 85% of pure tris-2-hydroxyethyl triazolidine-3,5-dione.

EXAMPLE 7

505 g of uracol was suspended in 1500 g of tetramethylene sulphone in a three-necked flask (test arrangement as in Example 6), followed by the addition of 10 g of tetraethyl ammonium chloride. A clear solution was formed by introducing ethylene oxide at 120° C. Another 303 g of uracol was suspended and, immediately a clear solution had formed, another 202 g of uracol was added. After a total of 1310 g of ethylene oxide had been introduced, the reaction mixture was concentrated in vacuo, ultimately at 120° C./0.2 mbar, giving 2354 g of a viscous liquid which, according to analysis by gas chromatography, contains 84.5% of pure tris-2-hydroxyethyl triazolidine-3,5-dione.

By dissolving the viscous liquid in a mixture of isopropanol and acetone, followed by cooling, it is possible to obtain a crystalline substance melting at 86° to 88° C. which, after recrystallisation from isopropanol for example, has a melting point of 90° C. and which, according to its IR-spectrum, is identical with the pure tris-2-hydroxyethyl triazolidine-3,5-dione of Example 1.

We claim:

1. Heterocyclic tris-hydroxyalkyl compounds of the formula

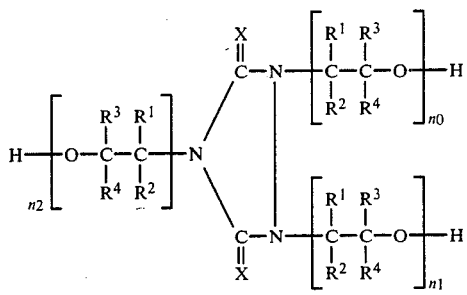

wherein
$n_0$, $n_1$ and $n_2$ are the same or different and each is an integer of from 1 to 30;
$R^1$, $R^2$, $R^3$ and $R^4$ are each hydrogen, methyl, or phenyl, with the proviso that not more than one can be phenyl and not more than two can be methyl,
and X is O or S.

2. Tris-hydroxyalkyl triazolidine-3,5-diones as claimed in claim 1 in which $n_0$, $n_1$ and $n_2$ each have a value of 1.

3. Tris-hydroxyalkyl triazolidine-3,5-diones as claimed in claim 1 wherein $R^1$, $R^2$, $R^3$ and $R^4$ each is hydrogen or methyl.

* * * * *